(12) United States Patent
Bundy et al.

(10) Patent No.: US 8,324,149 B2
(45) Date of Patent: Dec. 4, 2012

(54) ENCAPSIDATION OF HETEROLOGOUS ENTITIES INTO VIRUS-LIKE PARTICLES

(75) Inventors: Bradley C. Bundy, Mountain View, CA (US); James R. Swartz, Menlo Park, CA (US); Wei Chan, Sunnyvale, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 373 days.

(21) Appl. No.: 12/621,416

(22) Filed: Nov. 18, 2009

(65) Prior Publication Data

US 2010/0167981 A1  Jul. 1, 2010

Related U.S. Application Data

(60) Provisional application No. 61/115,828, filed on Nov. 18, 2008.

(51) Int. Cl.
*A61K 38/00* (2006.01)
(52) U.S. Cl. ...................................... 514/1.1
(58) Field of Classification Search ........................ None
See application file for complete search history.

(56) References Cited

U.S. PATENT DOCUMENTS

| | | | |
|---|---|---|---|
| 5,443,969 A | | 8/1995 | Wilson et al. |
| 5,677,124 A | | 10/1997 | DuBois et al. |
| 5,869,305 A | * | 2/1999 | Samulski et al. ............. 435/457 |
| 6,214,982 B1 | | 4/2001 | Pasloske et al. |
| 6,399,307 B1 | | 6/2002 | Pasloske et al. |
| 2002/0052040 A1 | * | 5/2002 | Hunt ......................... 435/235.1 |

OTHER PUBLICATIONS

Wu. Cell-Specific Delivery of Bacteriophage-Encapsidated Ricin A Chain. Bioconjugate Chem 15. vol. 6, pp. 587-595.*
Wu. Cell-Specific Delivery of Bacteriophage-Encapsidated Ricin A Chain. Bioconjugate Chem 1995, vol. 6, pp. 587-595.*
Katanaev; et al., "Formation of bacteriophage MS2 infectious units in a cell-free translation system", FEBS Letters (1996), 397:143-148.
Lingappa; et al., "Comparing capsid assembly of primate lentiviruses and hepatitis B virus using cell-free systems", Virology (2005), 333:114-123.
Loo; et al., "Encapsidation of Nanoparticles by Red Clover Necrotic Mosaic Virus", J. Am. Chem. Soc. (2007), 129 (36):11111-7.
Rulli; et al., "Selective and Nonselective Packaging of Cellular RNAs in Retrovirus Particles", Journal of Virology (2007), 81(12):6623-6631.
Wu; et al., "Delivery of antisense oligonucleotides to leukemia cells by RNA bacteriophage capsids", Nanomedicine (2005), 1:67-76.

* cited by examiner

*Primary Examiner* — Marcela M Cordero Garcia
(74) *Attorney, Agent, or Firm* — Bozicevic, Field & Francis LLP; Pamela J. Sherwood

(57) ABSTRACT

Methods are provided for the utilization of bacterial cell-free extracts in the synthesis of high yields of virus like particles with encapsidated cargo.

10 Claims, 6 Drawing Sheets

(SEQ ID NO:1)

ENCAPSIDATION OF HETEROLOGOUS ENTITIES INTO VIRUS-LIKE PARTICLES

BACKGROUND OF THE INVENTION

Virus like particles (VLPs) consist of viral proteins derived from the structural proteins of a virus, usually in the absence of a viral genome. VLPs have received considerable attention for vaccines, targeted drug delivery, targeted gene delivery, and nanotechnology applications. VLP vaccines that are currently approved by the Food and Drug Administration (FDA) include human papillomavirus and Hepatitis B vaccines, which are very effective at eliciting both T cell and B cell immune responses.

The vast majority of eukaryote-infecting-virus-based VLPs have been synthesized using the insect-cell-based baculovirus expression system or mammalian-cell-based protein expression systems. Although the synthesis of virus-like particles has been attempted in cell-free systems, yields have been extremely low in eukaryotic cell-free systems (Lingappa et al. 2005. Virology 333:114), and assembly has failed in conventional prokaryotic systems (Katanaev et al. 1996. FEBS 397:143).

Virus-like particle (VLP) vaccines are typically comprised of multiple copies of a protein that, when assembled together, mimic the conformation of a native virus. In the currently approved vaccines, the virus coat proteins themselves are the antigen of interest, and thus the virus protein is derived from the pathogen of interest. However, there has also been interest in using a VLP as a carrier for heterologous antigens, e.g. polypeptide antigens.

Encapsidation of exogeneous materials with a VLP has also been explored with viruses produced in cell culture. Loo et al. (2007) J Am Chem. Soc. 129(36):11111-7 report that small nanoparticles conjugated to an origin of assembly RNA sequence were encapsidated by red clover necrotic mosaic virus. In the absence of packageable viral RNA, assembly of retrovirus is still efficient, and the released virus-like particles still contain roughly normal amounts of RNA. It was also found that the retrovirus will non-selectively package mRNAs (Rulli et al. (2007) J. Virol. 81(12):6623-31).

Wu et al. (2005) Nanomedicine 1(1):67-76 report encapsidation of antisense oligonucleotides in MS2 bacteriophage capsid proteins. The oligonucleotides were synthesized as covalent extensions to the translational repressor/assembly initiation signal (TR), a 19 nt stem-loop, of the RNA phage MS2. The VLPs were constructed by soaking the oligonucleotides directly into recombinant RNA-free capsid shells.

Methods of encapsidating entities in VLPs are of great interest, particularly in combination with cell-free protein synthesis systems.

Relevant Literature

DuBois et al. U.S. Pat. No. 5,677,124, 1997; Wilson and Hwang-Lee, U.S. Pat. No. 5,443,969, 1995; Pasloske et al. U.S. Pat. No. 6,399,307, 2002; Pasloske et al., U.S. Pat. No. 6,214,982, 2001.

SUMMARY OF THE INVENTION

Methods are provided for selective packaging of exogenous entities (cargo) into virus-like particles (VLP) using cell-free protein synthesis. Packaged VLPs can be useful for a number of applications including vaccination, drug delivery, gene delivery, and diagnostic imaging. In the methods of the invention, a prokaryotic cell-free synthesis reaction is used to produce at least one viral coat protein, which self-assembles into a stable virus like particle, or capsid, in the presence of a cargo entity. The cargo can be directly added to the cell-free synthesis environment and the concentration directly controlled. In some embodiments the conditions for cell free protein synthesis are modified to decrease the concentration of undesirable, packagable nucleic acids, e.g. plasmid DNA, mRNA not associated with ribosomes, and the like, relative to conventional methods of cell free protein synthesis.

In some embodiments of the invention, the cargo is conjugated to the cognate viral polynucleotide packaging sequence, e.g. the MS2 pac sequence, the Qbeta packaging tag, etc. This packaging "tag" may be single or double stranded, and may be DNA or RNA, as appropriate for the virus.

Cargo of interest include small molecules, e.g. drugs, nanoparticles, e.g. metallic nanoparticles, anti-oxidants, luciferin, etc.; polypeptides, e.g. oligopeptides, proteins, etc.; polynucleotides, e.g. siRNA, antisense oligonucleotides, CpG containing oligonucleotides, etc. In some embodiments the cargo has a net negative charge, e.g. polynucleotides, acidic compounds, and the like.

In some embodiments of the invention, a cell free protein synthesis reaction is provided, where the reaction mix is supplemented with exogenous initiation factors. The addition of such initiation factors increases the efficiency of translation from mRNA molecules, thereby allowing comparable yields from reactions with decreased concentrations of plasmid DNA and mRNA. In some embodiments the reaction mix comprises decreased levels of plasmid DNA, relative to conventional reactions. In some embodiments the reaction mix is supplemented with each of a prokaryotic initiation factor 1, initiation factor 2 and initiation factor 3. In some embodiments, the cell free reaction mixture is utilized for selective packaging of exogenous entities (cargo) into virus-like particles (VLP).

DETAILED DESCRIPTION OF THE EMBODIMENTS

Figure 1:
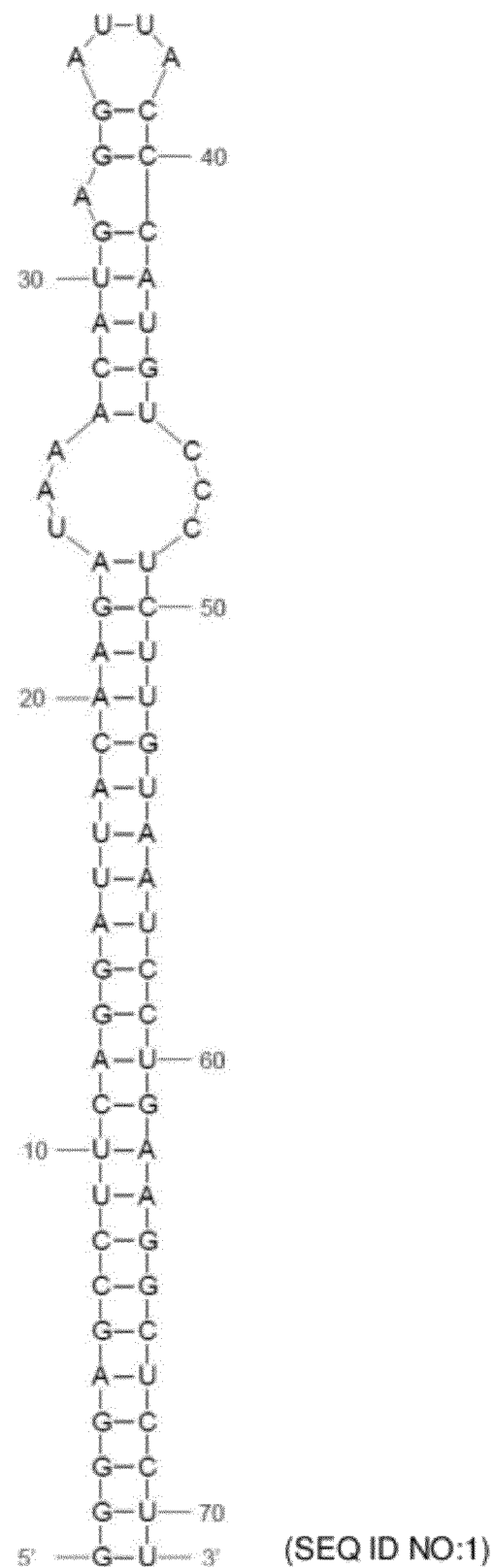
FIG. 1: Image of predicted hybridization of firefly luciferase shRNA with the MS2 TR sequence inserted (bases 27 through 45) as predicted by mfold (Zucker (2003) Nucleic Acids Res 31(13):3206-3415.).

Methods are provided for selective packaging of exogenous entities (cargo) into virus-like particles (VLP) using cell-free protein synthesis. In the methods of the invention, a prokaryotic cell-free synthesis reaction is used to produce at least one viral coat protein, which self-assembles into a stable virus like particle, or capsid, in the presence of a cargo entity. The cargo can be directly added to the cell-free synthesis environment and the concentration directly controlled. In some embodiments the conditions for cell free protein synthesis are modified to decrease the concentration of undesirable, packagable nucleic acids, e.g. plasmid DNA, mRNA not associated with ribosomes, and the like, relative to conventional methods of cell free protein synthesis.

The cell-free protein synthesis environment allows direct access to the coupled transcription/translation/VLP assembly environment. This direct access can be used for optimization of transcription, translation, VLP assembly and/or encapsidation into VLPs. In many cases it is desirable to encapsidate a synthetic or modified nucleic acid or protein or other entity into a VLP as "cargo". The cargo can be directly added to the cell-free synthesis environment and the concentration directly controlled. This is difficult, if not impossible, to do in vivo due to the cell wall barrier. VLPs produced using cell-free protein synthesis have a significantly lower probability of encapsulating non-targeted nucleic acid. The cell-free environment is more dilute than inside a cell. Also, in the cell-free environment endogenous RNA is not transcribed; only the desired RNA and protein are transcribed and translated. However, in vivo the cell is constantly producing many other RNAs and proteins at high concentrations which will compete with the desired cargo for encapsidation.

The cell-free system allows greater control of the transcription/translation environment and ease of VLP recovery and purification, as the system lacks a cell-wall and membrane components. For example, the redox potential, pH, and/or ionic strength can be altered which is necessary for optimum assembly, disassembly, and reassembly of many VLPs. In many cases where the VLP is synthesized in a cell, e.g. a bacterial cell, the capsid must be disassembled to purge any biomaterial encapsulated during the assembly process and reassembled in vitro to load the VLP with cargo. This is a lengthy and inefficient process. By using the cell-free transcription-translation system, the VLP production process is streamlined by eliminating the in vivo production step as well as the disassembly and reassembly.

For various purposes, including without limitation the selective packaging described herein, it is desirable to modify the conditions for cell free protein synthesis decrease the concentration of packagable nucleic acids, e.g. plasmid DNA, mRNA not associated with ribosomes, and the like. In some embodiments of the invention, the modification is achieved by supplementing the reaction mix with exogenous initiation factors to increase the efficiency of translation from mRNA molecules, usually accompanied by decreasing the levels of plasmid DNA, relative to conventional reactions. In some embodiments the reaction mix is supplemented with each of a prokaryotic initiation factor 1, prokaryotic initiation factor 2 and prokaryotic initiation factor 3, for example E. coli infA, infB and infC, the molecular characterization of which is well-known in the art. In some embodiments, the cell free reaction mixture is utilized for selective packaging of exogenous entities (cargo) into virus-like particles (VLP).

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Virus like particle. As used herein, the term "virus like particle" refers to a stable macromolecular assembly of one or more virus proteins, usually viral coat proteins. The number of separate protein chains in a VLP will usually be at least about 60 proteins, about 80 proteins, at least about 120 proteins, or more, depending on the specific viral geometry. In the methods of the invention, the cell-free synthesis reaction mixture provides conditions permissive for self-assembly into the capsid structure, even where the concentration of coat proteins may be dilute relative to the concentrations associated with in vivo viral synthesis, e.g. less than about 500 μg/ml, less than about 400 μg/ml, less than about 250 μg/ml. The methods of the invention provide for synthesis of the coat protein in the absence of the virus polynucleotide genome, and thus the capsid may be empty, or contain non-viral components, e.g. mRNA fragments, etc. The cell-free synthesis reaction mixtures of the present invention surprisingly provide conditions permissive for self-assembly of coat proteins into a capsid structure displaying helical or icosahedral symmetry.

A stable VLP maintains the association of proteins in a capsid structure under physiological conditions for extended periods of time, e.g. for at least about 24 hrs, at least about 1 week, at least about 1 month, or more. Once assembled, the VLP can have a stability commensurate with the native virus particle, e.g. upon exposure to pH changes, heat, freezing, ionic changes, etc. Additional components of VLPs, as known in the art, can be included within or disposed on the VLP. VLPs do not contain intact viral nucleic acids, and they are non-infectious. In some embodiments there is sufficient viral surface envelope glycoprotein and/or adjuvant molecules on the surface of the VLP so that when a VLP preparation is formulated into an immunogenic composition and administered to an animal or human, an immune response (cell-mediated or humoral) is raised.

Viruses can be classified into those with helical symmetry or icosahedral symmetry. Generally recognized capsid morphologies include: icosahedral (including icosahedral proper, isometric, quasi-isometric, and geminate or "twinned"), polyhedral (including spherical, ovoid, and lemon-shaped), bacilliform (including rhabdo- or bullet-shaped, and fusiform or cigar-shaped), and helical (including rod, cylindrical, and filamentous); any of which may be tailed and/or may contain surface projections, such as spikes or knobs.

In one embodiment of the invention, the coat protein is selected from the capsids of viruses classified as having any icosahedral morphology, and the VLP has an icosahedral geometry. Generally, viral capsids of icosahedral viruses are composed of numerous protein sub-units arranged in icosahedral (cubic) symmetry. Native icosahedral capsids can be built up, for example, with 3 subunits forming each triangular face of a capsid, resulting in 60 subunits forming a complete capsid. A representative of this small viral structure is bacteriophage ØX174. Many icosahedral virus capsids contain more than 60 subunits. Many capsids of icosahedral viruses contain an antiparallel, eight-stranded beta-barrel folding motif. The motif has a wedge-shaped block with four beta strands (designated BIDG) on one side and four (designated CHEF) on the other. There are also two conserved alpha-helices (designated A and B), one is between betaC and betaD, the other between betaE and betaF.

Virus coat proteins of interest include any of the known virus type, e.g. dsDNA viruses, such as smallpox (variola); vaccinia; herpesviruses including varicella-zoster; HSV1, HSV2, KSVH, CMV, EBV; adenovirus; hepatitis B virus; SV40; T even phages such as T4 phage, T2 phage; lambda phage; etc. Single stranded DNA viruses include phiX-174; adeno-associated virus, etc. Negative-stranded RNA viruses include measles virus; mumps virus; respiratory syncytial virus (RSV); parainfluenza viruses (PIV); metapneumovirus; rabies virus; Ebola virus; influenza virus; etc. Positive-stranded RNA viruses include polioviruses; rhinoviruses; coronaviruses; rubella; yellow fever virus; West Nile virus; dengue fever viruses; equine encephalitis viruses; hepatitis A and hepatitis C viruses; tobacco mosaic virus (TMV); etc. Double-stranded RNA viruses include reovirus; etc. Retroviruses include rous sarcoma virus; lentiviruses such as HIV-1 and HIV-2; etc.

Bacteriophages are of interest, e.g. the MS2 bacteriophage, the Q beta bacteriophage, etc. Myoviridae (phages with contractile tails) include mu-like viruses; P1-like viruses, e.g. P1; phiW39, etc.; P2-like viruses; SPO-1-like viruses; T4-like viruses; etc. Podoviridae (phages with short tails) include N4-like viruses; P22-like viruses, e.g. P22; phi-29-like viruses, e.g. phi-29; T7-like viruses, e.g. T3; T7; W31; etc. Siphoviridae (phages with long non-contractile tails) include c2-like viruses; L5-like viruses; Lambda-like viruses, e.g. phage lambda, HK022; HK97, etc.; N15-like viruses; PhiC31-like viruses; psiM1-like viruses; T1-like viruses, e.g. phage T1, etc. Microviridae (isometric ssDNA phages) include Chlamydiamicrovirus; Microvirus, e.g. phage alpha 3, phage WA13, etc.; phage G4; phage phiX174 and related coliphages. Many additional phages known to those of skill in the art remain unclassified. The sequence of many coat proteins are publicly available.

The nucleic acid sequence encoding the viral capsid or proteins can be modified to alter the formation of VLPs (see e.g. Brumfield, et al. (2004) J. Gen. Virol. 85: 1049-1053). For example, three general classes of modification are most typically generated for modifying VLP expression and assembly. These modifications are designed to alter the interior, exterior or the interface between adjacent subunits in the assembled protein cage. To accomplish this, mutagenic primers can be used to: (i) alter the interior surface charge of the viral nucleic acid binding region by replacing basic residues (e.g. K, R) in the N terminus with acidic glutamic acids (Douglas et al., 2002b); (ii) delete interior residues from the N terminus (in CCMV, usually residues 4-37); (iii) insert a cDNA encoding an 11 amino acid peptide cell-targeting sequence (Graf et al., 1987) into a surface exposed loop and (iv) modify interactions between viral subunits by altering the metal binding sites (in CCMV, residues 81/148 mutant).

The term "cargo" as used herein describes any molecule, e.g. nucleic acid, polypeptide, pharmaceutical, etc. with a desired biological activity and suitable solubility profile that is encapsidated into a VLP by the methods of the invention. The methods of the invention find particular use with active agents, e.g. nucleic acids, which have a short half-life in vivo due to degradation. In some embodiments the cargo has a net negative charge, e.g. polynucleotides, acidic compounds, and the like.

In some embodiments of the invention, the cargo is conjugated to the cognate viral polynucleotide packaging sequence, where the tag may be conjugated by any convenient chemistry, including polynucleotide synthesis or ligation. This packaging "tag" may be single or double stranded, and may be DNA or RNA, as appropriate for the virus. Exemplary packaging tags include those for MS2 and Q beta bacteriophage, and may be oligonucleotides of less than about 50 nt in length, less than 30 nt in length, and in some instances have a high degree of secondary structure, e.g. hairpins, stem loops and the like. Packaging sequences are known in the art, for example sequences are discussed, inter alia, by Iyer et al. Virus Res. 2006 April; 117(1):156-84; Poranen and Tuma Virus Res. 2004 April; 101(1):93-100; Mindich Virus Res. 2004 April; 101(1):83-92; Taraporewala and Patton Virus Res. 2004 April; 101(1):57-66; Davison et al. J Gen Virol. 2003 November; 84(Pt 11):2895-908; Brussow Annu Rev Microbiol. 2001; 55:283-303; Hendrix Cell. 1998 Jul. 24; 94(2):147-50; and Campbell Annu Rev Microbiol. 1994; 48:193-222.

Cargo of interest include, without limitation, pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Active agents encompass numerous chemical classes, though typically they are organic molecules, and may be biopolymers such as polypeptides and polynucleotides, or small organic compounds having a molecular weight of more than 50 and less than about 2,500 daltons. Agents are also found among biomolecules including peptides, saccharides, fatty acids, lipids, steroids, purines, pyrimidines, derivatives, structural analogs or combinations thereof.

Included in the active agents are genetic agents. As used herein, the term "genetic agent" refers to polynucleotides and analogs thereof. Genetic agents such as DNA can result in an introduced change in the genetic composition of a cell, e.g. through the integration of the sequence into a chromosome. Genetic agents such as antisense or siRNA oligonucleotides can also affect the expression of proteins without changing the cell's genotype, by interfering with the transcription or translation of mRNA. The effect of a genetic agent is to increase or decrease expression of one or more gene products in the cell.

A large number of public resources are available as a source of genetic sequences, e.g. for human, other mammalian, and human pathogen sequences. A substantial portion of the human genome is sequenced, and can be accessed through public databases such as Genbank. Resources include the uni-gene set, as well as genomic sequences. For example, see Dunham et al. (1999) *Nature* 402, 489-495; or Deloukas et al. (1998) *Science* 282, 744-746. cDNA clones corresponding to many human gene sequences are available from the IMAGE consortium. The international IMAGE Consortium laboratories develop and array cDNA clones for worldwide use. The clones are commercially available, for example from Genome Systems, Inc., St. Louis, Mo. Methods for cloning sequences by PCR based on DNA sequence information are also known in the art.

In one embodiment, the cargo is an antisense or siRNA sequence that acts to reduce expression of a targeted sequence. Antisense or siRNA nucleic acids are designed to specifically bind to RNA, resulting in the formation of RNA-DNA or RNA-RNA hybrids, with an arrest of DNA replication, reverse transcription or messenger RNA translation. Gene expression is reduced through various mechanisms. Antisense nucleic acids based on a selected nucleic acid sequence can interfere with expression of the corresponding gene.

Antisense oligonucleotides (ODN), include synthetic ODN having chemical modifications from native nucleic acids, or nucleic acid constructs that express such anti-sense molecules as RNA. One or a combination of antisense molecules may be administered, where a combination may comprise multiple different sequences. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

Among nucleic acid oligonucleotides are included phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'—NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Also of interest are RNAi agents. RNAi agents are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

Polypeptides of interest include biologically active proteins, e.g. transcription factors, proteins involved in signaling pathways, cytokines, chemokines, toxins, and the like.

Other agents of interest include detectable markers, e.g. luciferase, luciferin, green fluorescent proteins, fluorochromes, e.g. FITC, etc., and the like. Detectable markers may also include imaging entities, e.g. metallic nanoparticles such as gold, platinum, silver, etc., which may be provided as nanoparticles, usually nanoparticles of less than 10 nm, less then about 5 nm, etc.

In vitro synthesis, as used herein, refers to the cell-free synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art.

The concentration of cargo in the reaction mix will be determined by the specific composition of the cargo. In some embodiments, the cargo is present at a concentration of at least about 1 µM, at least about 10 µM, at least about 100 µM, at least about 1 mM. The plasmid DNA in the reaction mix is optionally reduced by about 2-fold relative to conventional synthetic reactions, and may be reduced by about 5-fold, by about 10-fold, or more. In some embodiments, the virus structural proteins and synthetic mix are modified to provide for inclusion of unnatural amino acids, for example as described by WO 2008/066583, the disclosure of which is herein specifically incorporated by reference.

One or more exogenous initiation factors may be added to the reaction mix to improve efficiency of translation. Usually the exogenous factors are initiation factor 1, initiation factor 2 and inititaiton factor 3, although the specific number may vary with the microorganism from which the biological extract is obtained. Where the extract is obtained from *E. coli*, the initiation factors may be infA, infB and infC, each is which may be added to a concentration of at least about 0.1 µM, at least about 0.5 µM, at least about 1 µM, at least about 5 µM, and not more than about 50 µM, usually not more than about 10 µM. The addition of the initiation factors allows a decrease in the input plasmid DNA in the reaction mix, e.g. providing not more than about 2.5 nM plasmid DNA, not more than about 1 nM, and may be not more than about 0.5 nM plasmid DNA.

In some embodiments of the invention, cell free synthesis is performed in a reaction where oxidative phosphorylation is activated, e.g. the CYTOMIM™ system. The activation of the respiratory chain and oxidative phosphorylation is evidenced by an increase of polypeptide synthesis in the presence of $O_2$. In reactions where oxidative phosphorylation is activated, the overall polypeptide synthesis in presence of $O_2$ is reduced by at least about 40% in the presence of a specific electron transport chain inhibitor, such as HQNO, or in the absence of $O_2$. The reaction chemistry may be as described in international patent application WO 2004/016778, herein incorporated by reference.

The CYTOMIM™ environment for synthesis utilizes cell extracts derived from bacterial cells grown in medium containing glucose and phosphate, where the glucose is present initially at a concentration of at least about 0.25% (weight/volume), more usually at least about 1%; and usually not more than about 4%, more usually not more than about 2%. An example of such media is 2YTPG medium. However one of skill in the art will appreciate that many culture media can be adapted for this purpose, as there are many published media suitable for the growth of bacteria such as *E. coli*, using both defined and undefined sources of nutrients (see Sambrook, J., E. F. Fritsch, and T. Maniatis. 1989. Molecular Cloning: A Laboratory Manual, $2^{nd}$ edition. Cold Spring Harbor University Press, Cold Spring Harbor, N.Y. for examples of glucose containing media). Alternatively, the culture may be grown using a protocol in which the glucose is continually fed as required to maintain a high growth rate in either a defined or complex growth medium.

The reaction mixture may be supplemented by the inclusion of vesicles, e.g. an inner membrane vesicle solution. Where provided, such vesicles may comprise from about 0 to about 0.5 volumes, usually from about 0.1 to about 0.4 volumes.

In the reaction mix PEG will usually be present in not more than trace amounts, for example less than 0.1%, and may be less than 0.01%. Reactions that are substantially free of PEG contain sufficiently low levels of PEG that, for example, oxidative phosphorylation is not PEG-inhibited, and the self-assembly of virus-like particles is not inhibited. The molecules spermidine and putrescine may be used in the place of PEG. Spermine or spermidine is present at a concentration of at least about 0.5 mM, usually at least about 1 mM, preferably about 1.5 mM, and not more than about 2.5 mM. Putrescine is present at a concentration of at least about 0.5 mM, preferably at least about 1 mM, preferably about 1.5 mM, and not more than about 2.5 mM. The spermidine and/or putrescine may be present in the initial cell extract or may be separately added.

The concentration of magnesium in the reaction mixture affects the overall synthesis. Often there is magnesium present in the cell extracts, which may then be adjusted with additional magnesium to optimize the concentration. Sources of magnesium salts useful in such methods are known in the art. In one embodiment of the invention, the source of magnesium is magnesium glutamate. A preferred concentration of magnesium is at least about 5 mM, usually at least about 10 mM, and preferably a least about 12 mM; and at a concentration of not more than about 25 mM, usually not more than about 20 mM. Other changes that may enhance synthesis include the omission of HEPES buffer and phosphoenol pyruvate from the reaction mixture.

The system can be run under aerobic and anaerobic conditions. Oxygen may be supplied, particularly for reactions larger than 15 µl, in order to increase synthesis yields. The headspace of the reaction chamber can be filled with oxygen; oxygen may be infused into the reaction mixture; etc. Oxygen can be supplied continuously or the headspace of the reaction chamber can be refilled during the course of protein expression for longer reaction times. Other electron acceptors, such as nitrate, sulfate, or fumarate may also be supplied in conjunction with preparing cell extracts so that the required enzymes are active in the cell extract.

It is not necessary to add exogenous cofactors for activation of oxidative phosphorylation. Compounds such as nicotinamide adenine dinucleotide (NADH), $NAD^+$, or acetyl-coenzyme A may be used to supplement protein synthesis yields but are not required. Addition of oxalic acid, a metabolic inhibitor of phosphoenolpyruvate synthetase (Pps), may be beneficial in increasing protein yields, but is not necessary.

The template for cell-free protein synthesis can be either mRNA or DNA, preferably a combined system continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally present at a concentration of at least about 50 mM, and not more than about 250 mM. Ammonium may be present, usually at a concentration of not more than 200 mM, more usually at a concentration of not more than about 100 mM. Usually, the reaction is maintained in the range of about pH 5-10 and a temperature of about 20°-50° C.; more usually, in the range of about pH 6-9 and a temperature of about 25°-40° C. These ranges may be extended for specific conditions of interest.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Biological extracts. For the purposes of this invention, biological extracts are any preparation comprising the components of protein synthesis machinery, usually a bacterial cell extract, wherein such components are capable of expressing a nucleic acid encoding a desired protein. Thus, a bacterial extract comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, $N^{10}$-formyltetrahydrofolate, formylmethionine-tRNAf$^{Met}$ synthetase, peptidyl transferase, initiation factors such as IF-1, IF-2 and IF-3, elongation factors such as EF-Tu, EF-Ts, and EF-G, release factors such as RF-1, RF-2, and RF-3, and the like.

In a preferred embodiment of the invention, the reaction mixture comprises extracts from bacterial cells, e.g. *E. coli* S30 extracts, as is known in the art. For convenience, the organism used as a source of extracts may be referred to as the source organism. Methods for producing active extracts are known in the art, for example they may be found in Pratt (1984), Coupled transcription-translation in prokaryotic cell-free systems, p. 179-209, in Hames, B. D. and Higgins, S. J. (ed.), Transcription and Translation: A Practical Approach, IRL Press, New York. Kudlicki et al. (1992) *Anal Biochem* 206(2):389-93 modify the S30 *E. coli* cell-free extract by collecting the ribosome fraction from the S30 by ultracentrifugation. While such extracts are a useful source of ribosomes and other factors necessary for protein synthesis, they can also contain small amounts of enzymes responsible for undesirable side-reactions that are unrelated to protein synthesis, but which modulate the oxidizing environment of the reaction, and which can act to reduce the groups on the nascent polypeptide and the redox buffer.

Vesicles are optionally added to the reaction mix. Vesicles may purified from the organism from which the extract is derived (see Muller and Blobel (1984) "In vitro translocation of bacterial proteins across the plasma membrane of *Escherichia coli*", PNAS 81:7421-7425); or isolated from any other suitable cell, e.g. mammalian cells including cells from the species of target protein; or synthetic. Vesicles are typically added at a concentration of 0.1 to 5 mg/ml lipids, more preferably about 0.4 to 2.5 mg/ml. Vesicles may be purified by sucrose density gradient centrifugation or by other means known in the art. Vesicle preparation methods include, without limitation: homogenization, French press, extrusion, freeze/thaw, sonication, osmotic lysis, lysozyme/EDTA treatment, and the like. Other components that affect membrane protein insertion or folding may be added to the cell-free reaction mixture, including SRP, Ffh, 4.5S RNA, FtsY, and SecA. Also, other components may be added to the reaction such as specific enzymes and their substrates as required for capsid protein modification and capsid assembly.

Methods for Synthesis

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

The reactions may be of any volume, either in a small scale, usually at least about 1 μl and not more than about 15 μl, or in a scaled up reaction, where the reaction volume is at least about 15 μl, usually at least about 50 μl, more usually at least about 100 μl, and may be 500 μl, 1000 μl, or greater. In most cases, individual reactions will not be more than about 10 ml, although multiple reactions can be run in parallel. However, in principle, reactions may be conducted at any scale as long as sufficient oxygen (or other electron acceptor) is supplied when needed.

In addition to the above components such as cell-free extract, genetic template, and amino acids, materials specifically required for protein synthesis may be added to the reaction. These materials include salts, folinic acid, cyclic AMP, inhibitors for protein or nucleic acid degrading enzymes, inhibitors or regulators of protein synthesis, adjusters of oxidation/reduction potential(s), non-denaturing surfactants, buffer components, spermine, spermidine, putrescine, etc.

The salts preferably include potassium, magnesium, and ammonium salts (e.g. of acetic acid or glutamic acid). One or more of such salts may have an alternative amino acid as a counter anion. There is an interdependence among ionic species for optimal concentration. These ionic species are typically optimized with regard to protein production. When changing the concentration of a particular component of the reaction medium, that of another component may be changed accordingly. For example, the concentrations of several components such as nucleotides and energy source compounds may be simultaneously adjusted in accordance with the change in those of other components. Also, the concentration levels of components in the reactor may be varied over time. The adjuster of oxidation/reduction potential may be dithiothreitol, ascorbic acid, glutathione, cysteine, and/or their oxidized forms.

In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein and particles are accumulated in the reactor, and then are isolated and purified according to the usual method for protein purification after completion of the system operation. Product may also be continuously isolated, for example by affinity adsorption from the reaction mixture either in situ or in a circulation loop as the reaction fluid is pumped past the adsorption matrix.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump or by applying transmembrane pressure using other methods known in the art. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein or particle may include a unit packed with particles coated with antibody molecules or other molecules immobilized with a component for adsorbing the synthesized, desired product. Preferably, the product isolating means comprises two columns for alternating use.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity. Particle assembly may similarly be measured by methods known in the art; for example, by the use of sucrose density centrifugation analysis.

Another method of measuring the amount of protein produced in coupled in vitro transcription and translation reactions is to perform the reactions using a known quantity of radiolabeled amino acid such as $^{35}$S-methionine, $^{3}$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Kits for the practice of the subject methods may also be provided. Such kits may include bacterial extracts for protein synthesis, buffers appropriate for reactions where oxidative phosphorylation is activated, and suitable vectors.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

We have demonstrated the encapsidation of exogenous nucleic acid in MS2 VLPs produced using cell-free protein syntheses. The MS2 RNA pac sequence attached to a fluorophore (single-stranded O-methyl RNA of sequence 5'-ACAUGAGGAUUACCCAUGU-3' (SEQ ID NO:3) with 6-FAM™ at the 5' end synthesized by Integrated DNA technologies, inc. Coralville, Iowa) was added directly to the PANOxSP cell-free reaction at time points 0, 15, 30 and 45 minutes increasing the concentration by 9.1 µM each time. By sucrose gradient velocity sedimentation, it was determined that 68% assembly into VLPs occurred and 239 µg/mL of MS2 coat protein was produced. A Mithras LB 940 fluorometer (Berthold Technologies LLC, Oak Ridge, Tenn.) was used to determine the amount of RNA-fluorophore incorporated into the VLP as compared to a linear concentration gradient of the RNA-fluorophore. An average of 2.2 RNA-fluorophores were encapsidated into each MS2 VLP. Other procedures including cell-free reaction conditions and the purification method were described previously (Bundy and Swartz (2008) Biotechnol Bioeng 100(1):28-37).

Example 2

We have also demonstrated encapsidation of shRNA into virus-like particles produced using cell-free protein synthesis. A firefly luciferase shRNA was extended to contain the MS2 packaging sequence (MS2 bacteriophage TR (translational operator) RNA sequence which serves as a pac sequence for the virus).

This shRNA-MS2TR RNA sequence as shown in FIG. 1 was synthesized in an in vitro transcription reaction at 37° C. which was identical to the PANOxSP cell-free reaction described previously except E. coli extract and plasmid DNA were not added and the following components were added: 10 mM dithiothreitol, 1 U/uL RNAseOUT RNAse inhibitor (Qiagen, Germantown, Md.), 10 mM potassium phosphate, hybridized synthetic oligonucleotides as described below, and recombinant T7 RNA polymerase was increased 4-fold. As described previously (Gondai et al. (2008) Nucleic Acids Res 36(3):e18), the following synthetic oligonucleotides served as the template for the above transcription reaction after they were hybridized by heating the mixture of oligonucleotides to 95° C. and cooling slowly: 5'-AAGGAGCCT-TCAGGATTACAAGAGGGACATGGG-TAATCCTCATGTTTATC TTGTAATCCTGAAGGCTCCCCTATAGT-GAGTCGTATTAATTTC-3' (SEQ ID NO:4) and 5'-GAAAT-TAATACGACT CACTATA-3' (SEQ ID NO:5) (Integrated DNA Technologies, Inc., Coralville, Iowa).

Figure 2:
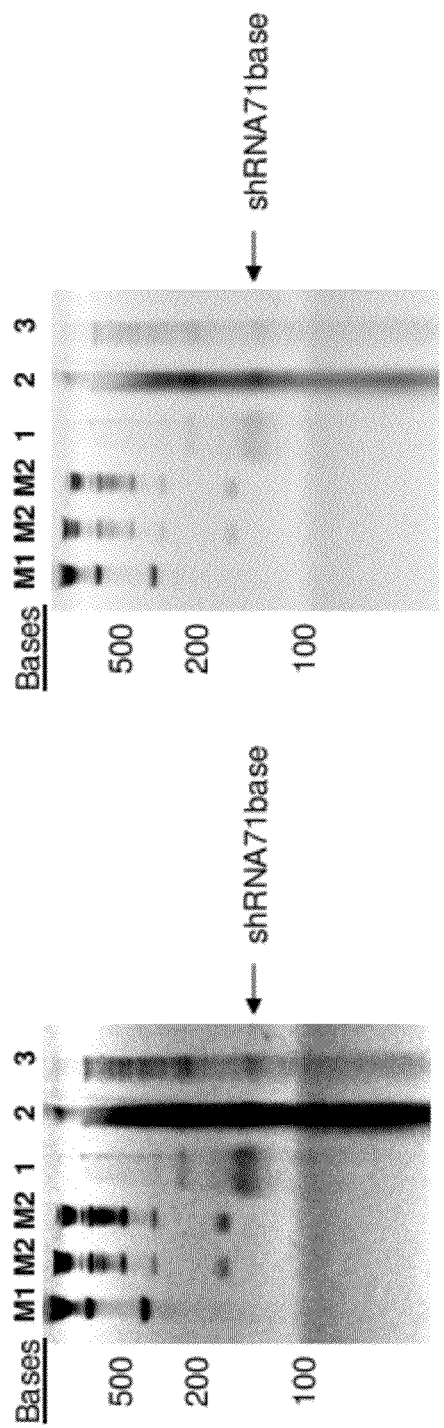
FIG. 2: 6% polyacrylamide TBE-Urea gels visualized with ethidium bromide. Lane M1: 0.2-10 kb Perfect RNA Marker; Lane M2: 2-Log DNA ladder; Lane 1: Product of in vitro transcription reaction producing firefly luciferase shRNA with MS2TR sequence inserted; Lane 2: Nucleic Acid extracted from purified CFPS-produced VLPs; Lane 3: 20-fold dilution of lane 2. Left and Right images are from the same gel visualized using difference contrasts.

After incubation at 37° C. for 1 hr, the products from the transcription reaction were added directly to the PANOxSP cell-free protein synthesis reaction at 37° C. for 3 hr and synthesized VLPs were purified as described previously (Bundy and Swartz 2008). Nucleic Acid was extracted from the purified VLPs using UltraPure Phenol:Chloroform: Isoamyl Alcohol (25:24:1, v/v) (Invitrogen Corp. Carlsbad, Calif.) and analyzed by electrophoresis using 6% polyacrylamide TBE-Urea gels (Invitrogen) per the manufacturer's specifications (FIG. 2). The shRNA-MS2TR represented approximately 9% of the encapsulated nucleic acid based on densitometry using ImageJ software (available at http://rsb.info.nih.gov/ij; developed by WayneRasband, National Institutes of Health, Bethesda, Md.).

Example 3

We have demonstrated that by supplementing a reaction described above with 8 µM of each initiation factor (IF1, IF2, and IF3) and by reducing the template plasmid concentration to 1 nM, we can reduce the encapsidation of mRNA produced during the course of cell free protein synthesis of the Q beta phage VLP and increase the encapsidation of exogenous cargo (desired nucleic acids or other cargo) in the Q beta phage VLP. In this example, DNA fused to a fluorophor was encapsidated.

The initiation factors were expressed using a T7 promoter as N-terminal hexa-histidine tagged (his-tag) proteins with a TEV protease cleavage site between the initiation factors (IFs) and the his-tag. The expression strain was BL21(DE3) E. coli. Expression was induced by 1 mM IPTG. After induction, the E. coli cells were harvested and lysed with a high pressure homogenizer. The IF his-tag fusion proteins were purified from the lysate using HisTrap columns (Manufactured by General Electric HealthCare, Piscataway, N.J.). The N-terminal his-tag was removed by treating the fusion with TEV protease, producing native form IFs. The IFs in the protease reaction were then purified using a HisTrap column, where the his-tag and the TEV protease (which also contained a his-tag motif) were bound to the column and the IFs flowed through the column since the IFs no longer had a his-tag motif.

The encapsidation of exogenous DNA into the Q beta phage VLP has been shown to be in competition with the encapsidation of mRNA into the VLP. To improve the encapsidation of the exogenous DNA into the Q beta phage VLP, we modified the cell-free reaction solution to reduce the amount of mRNA encapsidated in the VLP by reducing the concentration of the DNA template. Since this also reduced the quantity of protein produced by reducing the quantity of available messenger RNA, translation initiation factors were added to allow the mRNA to be more effectively used.

To quantify the amount of mRNA encapsidated into the VLP, the mRNA synthesized during the reaction was radioactively labeled with tritiated uridine by adding 2.8 μM tritiated uridine triphosphate into the cell free protein synthesis reaction. After the reaction, the assembled Q beta VLP was purified using sucrose gradient sedimentation. We determined the amount of mRNA encapsidated in the purified VLP by measuring the radioactivity of the VLP sample, since all radioactivity comes from the tritiated uridine incorporated into the mRNA. In order to find the number of mRNA molecules per VLP, we also quantified the amount of VLP capsid protein produced. This was done by labeling the protein with 14-C leucine by adding 5 μM 14-C leucine into a separate and parallel cell free protein synthesis reaction. After the reaction, the assembled Q beta VLP was purified using sucrose gradient sedimentation. We calculated the amount of assembled VLP by measuring the radioactivity of the VLP sample, since all radioactivity comes from the 14-C leucine incorporated into the VLP capsid protein. All measurements of radioactivity were performed using Beckman LS3801 Liquid Scintillation Counter (Beckman Coulter, Inc., Fullerton, Calif.).

Figure 3:
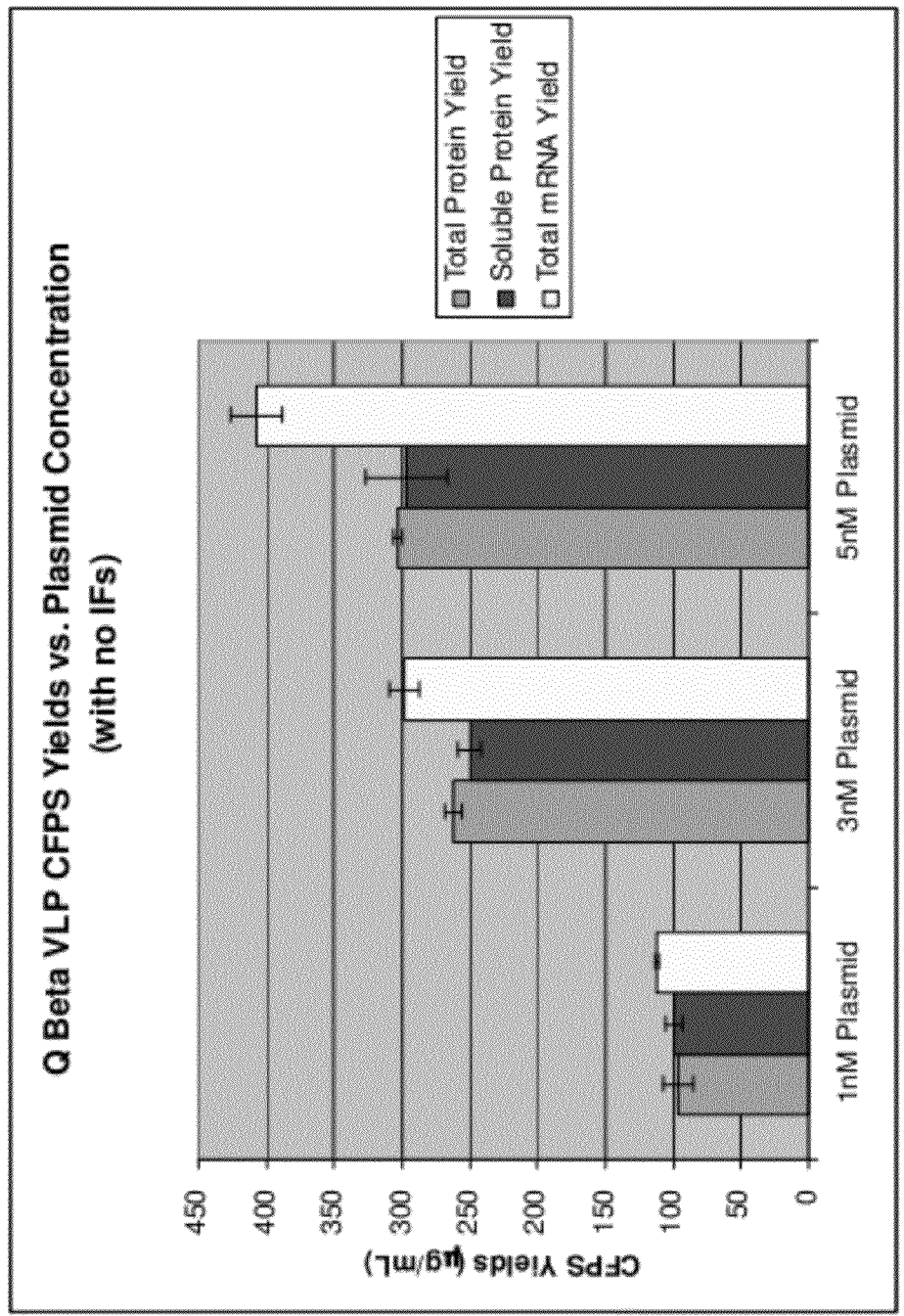
FIG. 3: Cell Free Protein Synthesis Yields (Total Protein, Soluble Protein, Total mRNA) as a function of plasmid concentration with no addition of IFs.
Figure 4:
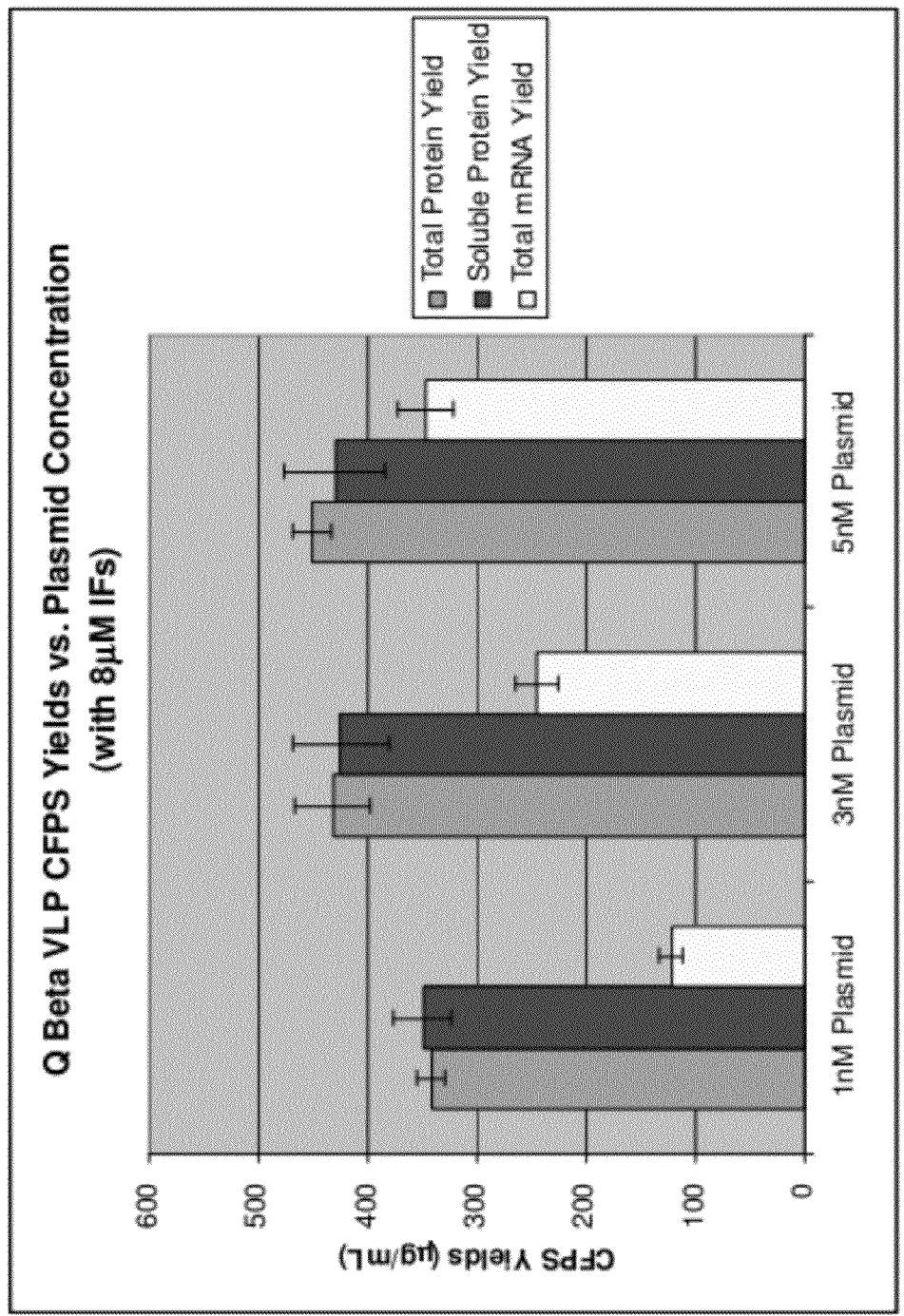
FIG. 4: Cell Free Protein Synthesis Yields (Total Protein, Soluble Protein, Total mRNA) as a function of plasmid concentration with the addition of 8 µM IFs.

FIG. 3 shows that the reduction of template plasmid concentration decreases the total amount of mRNA produced as well as decreases the amount of protein produced. FIG. 4 shows that with the addition of 8 μM IFs, the total amount of mRNA produced can be reduced while maintaining high levels of protein production. In the presence of 8 μM IFs, reducing plasmid concentration from 5 nM to 1 nM reduces the average number of encapsidated mRNA per VLP from 11.1 to 7.6, a 31% decrease.

Figure 5:
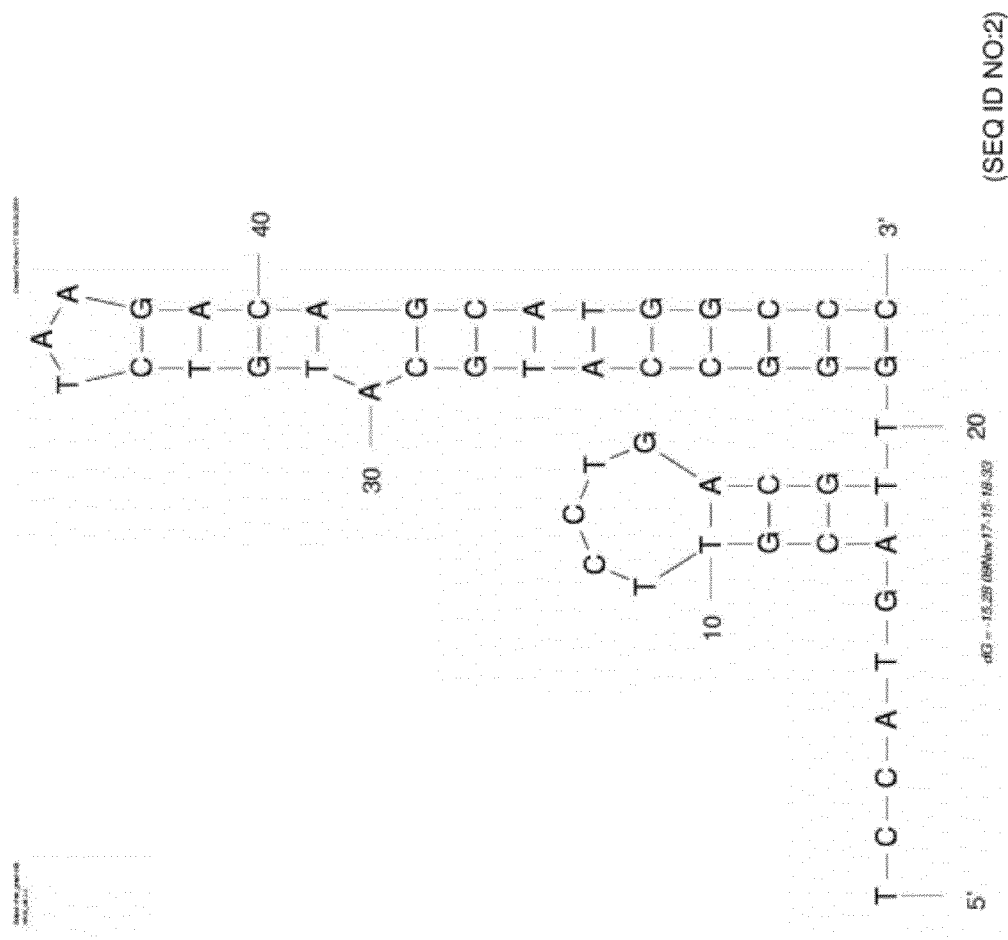
FIG. 5: Image of predicted hybridization of the CpG DNA (bases 1 to 20) with the Q beta phage TR sequence (bases 26 through 45) as predicted by Mfold (Zucker (2003) Nucleic Acids Res 31(13):3206-3415.).
Figure 6:
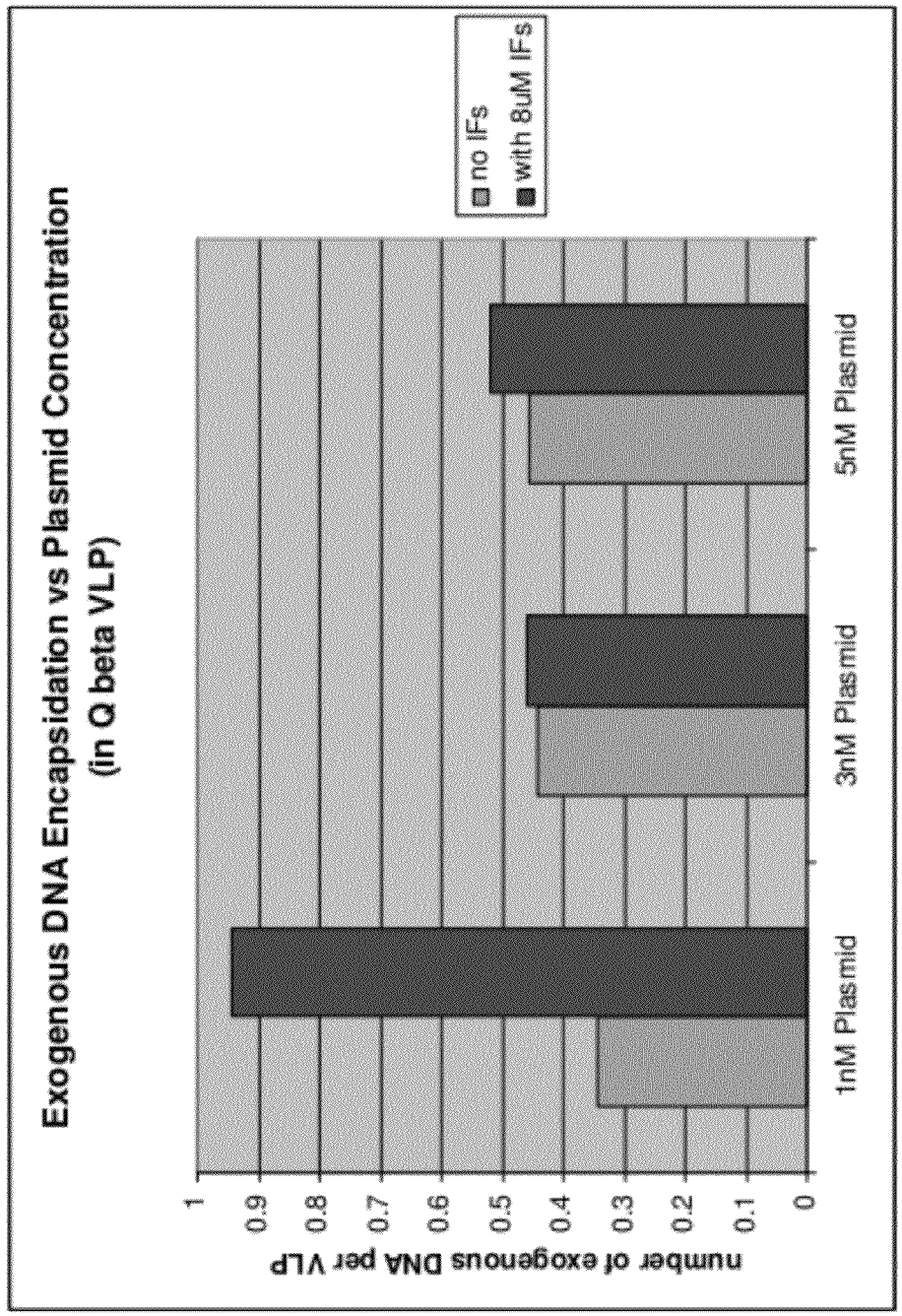
FIG. 6: Amount of exogenous DNA encapsidated as a function of plasmid concentration in the absence and presence of 8 µM IFs.

The encapsidation of exogenous DNA into the Q beta phage VLP was then characterized. The exogenous DNA shown in FIG. 5 was synthesized by Integrated DNA technologies, inc. Coralville, Iowa and a fluorophore (6-FAM) was attached at the 3' end. This compound was added into the cell free reaction mix at a concentration of 4.3 nM at the beginning of the reaction. After the reaction, the assembled Q beta VLP was purified using sucrose gradient sedimentation. We determined the amount of exogenous DNA encapsidated in the purified VLP by measuring the fluorescence of the VLP sample, since all fluorescence comes from the exogenous DNA labeled with 6-FAM. A Mithras LB 940 fluorimeter (Berthold Technologies LLC, Oak Ridge, Tenn.) was used to measure the fluorescence, and the amount of exogenous DNA was calculated by comparing the VLP sample fluorescence to a linear concentration gradient of the DNA-fluorophore. With the addition of 8 μM IFs and the reduction of template plasmid concentration, we determined that the encapsidation of exogenous DNA was on average 0.94 DNA per Q beta phage VLP, a 50% increase in encapsidation efficiency compared to cell free reactions without the modifications (FIG. 6).

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for synthesis of virus like particles comprising encapsidated cargo in a cell-free in vitro reaction, the method comprising:
synthesizing virus coat proteins in a prokaryotic cell-free in vitro translation reaction in the presence of heterologous cargo;
wherein the virus coat proteins self-assemble into a stable virus like particle comprising at least 60 separate proteins; which VLP is free of a viral genome and comprises encapsidated metallic nanoparticle imaging agent.

2. The method of claim 1, wherein said virus coat protein is a bacteriophage coat protein.

3. The method of claim 2, wherein said bacteriophage is MS2.

4. A method for synthesis of virus like particles comprising encapsidated cargo in a cell-free in vitro reaction, the method comprising:
synthesizing virus coat proteins in a prokaryotic cell-free in vitro translation reaction in the presence of heterologous cargo wherein said prokaryotic cell-free in vitro translation reaction comprises exogenous translation initiation factors;
wherein the virus coat proteins self-assemble into a stable virus like particle comprising at least 60 separate proteins; which VLP is free of a viral genome and comprises encapsidated heterologous cargo.

5. The method of claim 4, wherein said exogenous translation initiation factors are infA, infB and infC, each at a concentration of at least about 1 μM.

6. The method of claim 5, wherein said prokaryotic cell-free in vitro translation reaction comprises plasmid DNA at a concentration of not more that about 2.5 nM.

7. The method according to claim 1 wherein said protein synthesis is performed in a reaction mixture comprising exogenous initiation factors at a concentration of at least about 1 nM, and plasmid DNA at a concentration of not more than about 2.5 nM.

8. The method of claim 4, wherein the heterologous cargo is a metallic nanoparticle imaging agent.

9. The method of claim 4, wherein said virus coat protein is a bacteriophage coat protein.

10. The method of claim 9, wherein said bacteriophage is MS2.

* * * * *

SEQUENCE LISTING

<160> NUMBER OF SEQ ID NOS: 5

<210> SEQ ID NO 1
<211> LENGTH: 71
<212> TYPE: RNA
<213> ORGANISM: Artificial Sequence
<220> FEATURE:
<223> OTHER INFORMATION: Synthetic ribonucleotide

<400> SEQUENCE: 1
ggggagccuu caggauuaca agauaaacau gaggauuacc caugcccuc uuguaauccu      60 gaaggcuccu u                                                          71

<210> SEQ ID NO 2
<211> LENGTH: 50
<212> TYPE: DNA
<213> ORGANISM: Artificial Sequence
<220> FEATURE:
<223> OTHER INFORMATION: Synthetic nucleotide

<400> SEQUENCE: 2
tccatgacgt tcctgacgtt gggccatgca tgtctaagac agcatggccc                50

```
<210> SEQ ID NO 3
<211> LENGTH: 19
<212> TYPE: RNA
<213> ORGANISM: Artificial Sequence
<220> FEATURE:
<223> OTHER INFORMATION: Synthetic ribonucleotide

<400> SEQUENCE: 3
acaugaggau uacccaugu                                               19

<210> SEQ ID NO 4
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 4
aaggagcctt caggattaca agagggacat gggtaatcct catgtttatc ttgtaatcct    60
gaaggctccc ctatagtgag tcgtattaat ttc                                 93

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
gaaattaata cgactcacta ta                                             22
```